(12) United States Patent
Humphreys et al.

(10) Patent No.: US 6,753,536 B2
(45) Date of Patent: Jun. 22, 2004

(54) APPARATUS FOR NEUTRALIZING CHEMICAL AND BIOLOGICAL THREATS

(76) Inventors: Wesley G. Humphreys, 2090 Waller Dr., Huntingdon Valley, PA (US) 19006; Wesley E. Humphreys, 2090 Waller Dr., Huntingdon Valley, PA (US) 19006

(*) Notice: Subject to any disclaimer, the term of this patent is extended or adjusted under 35 U.S.C. 154(b) by 0 days.

(21) Appl. No.: 10/305,539

(22) Filed: Nov. 27, 2002

(65) Prior Publication Data

US 2004/0099812 A1 May 27, 2004

Related U.S. Application Data

(60) Provisional application No. 60/338,783, filed on Dec. 5, 2001, and provisional application No. 60/333,508, filed on Nov. 28, 2001.

(51) Int. Cl.[7] .................................................. A61N 5/06
(52) U.S. Cl. .................. 250/455.11; 232/31; 250/454.1
(58) Field of Search ...................... 250/455.11, 454.1, 250/455.1; 422/24

(56) References Cited

U.S. PATENT DOCUMENTS

| | | | |
|---|---|---|---|
| 4,786,812 A | | 11/1988 | Humphreys |
| 4,866,282 A | * | 9/1989 | Miripol et al. ......... 250/455.11 |
| 4,896,042 A | | 1/1990 | Humphreys |
| 4,952,812 A | * | 8/1990 | Miripol et al. ......... 250/455.11 |
| 5,120,499 A | * | 6/1992 | Baron ......................... 422/24 |
| 5,130,553 A | | 7/1992 | Amoh |
| 5,459,322 A | * | 10/1995 | Warkentin ............. 250/455.11 |
| 6,165,526 A | * | 12/2000 | Newman ..................... 426/248 |
| 6,245,570 B1 | | 6/2001 | Grimm et al. |
| 6,576,188 B1 | * | 6/2003 | Rose et al. .................. 422/20 |
| 2003/0127506 A1 | * | 7/2003 | Braun ........................ 232/31 |

* cited by examiner

Primary Examiner—John R. Lee
Assistant Examiner—Johnnie L. Smith, II
(74) Attorney, Agent, or Firm—Michael G. Crilly, Esq.

(57) ABSTRACT

The present invention is an apparatus having a slidably disposed tray enabling the insertion of a contaminated object into and the removal of the same object after decontamination from the apparatus. In preferred embodiments, a handle is attached to the slidable tray allowing the user to manually extend and retract the receptacle from the apparatus. In alternate embodiments, the receptacle is mechanically extended and retracted via a motor. A switch is fixed to the apparatus thereby contacting the receptacle so as to activate and deactivating lamps based on the position of the tray. Germicidal and thermal lamp are provided to neutralize chemical agents and biological organisms adhered to an object. In alternate embodiments, lamp energy is redirected onto an object via one or more contoured reflectors.

9 Claims, 12 Drawing Sheets

Section A-A

Section A-A

Section B-B

Section C-C

APPARATUS FOR NEUTRALIZING CHEMICAL AND BIOLOGICAL THREATS

CROSS REFERENCE TO RELATED APPLICATIONS

This application claims benefit under 35 U.S.C. 119(e) from U.S. Provisional Application No. 60/333,508 filed on Nov. 28, 2001 and U.S. Provisional Application No. 60/338,783 filed on Dec. 5, 2001.

BACKGROUND OF THE INVENTION

1. Field of the Invention

The present invention generally relates to an apparatus for the neutralization of chemical and biological threats. Specifically, the invention provides a slidable tray facilitating insertion and removal of an object from a decontamination chamber. Apparatus design includes lamps and lamp-reflector embodiments so as to neutralize chemical and/or biological agents contaminating an object.

2. Description of Related Art

The proliferation of technology and materials enabling the manufacture of weapons of mass destruction creates an unprecedented likelihood that civilian populations will be exposed to chemical agents and biological organisms. The likelihood of exposure to weapons traditionally directed against military personnel is further amplified by rather unconventional delivery systems, one example being mail.

The related arts include two portable devices described and claimed by Wesley G. Humphreys. In U.S. Pat. No. 4,786,812 issued on Nov. 22, 1988, Humphreys provides a single-piece, hand-held device facilitating the sterilization of a surface contaminated with mold, yeast or virus. Sterilization is achieved via ultraviolet (UV) lamps operating at a wavelength of 253.7 nanometers. The invention further sterilizes the surrounding atmosphere by providing a fan so as to draw an airstream across the UV lamps. Later in U.S. Pat. No. 4,896,042 issued on Jan. 23, 1990, Humphreys provides a two-piece device consisting of a hand-held unit with UV lamps for the sterilization of surfaces and a base unit with fan onto which the hand-held unit is secured for the sterilization of the surrounding atmosphere. This invention is specifically designed to prevent the insertion of objects between hand-held and base units.

Neither invention provides for the contained decontamination of high-risk items, namely mail, money, or other commonly encountered objects. Neither invention provides for the neutralization of both chemical and biological threats.

What is currently required is a device that allows an individual with little or no formal training related to chemical and biological threats to effectively decontaminate high-risk items in a contained and easily controllable fashion.

BRIEF DESCRIPTION OF THE DRAWINGS

The invention will now be described in more detail, by way of example only, with reference to the accompanying drawings, in which.

REFERENCE NUMERALS

Figure 1:
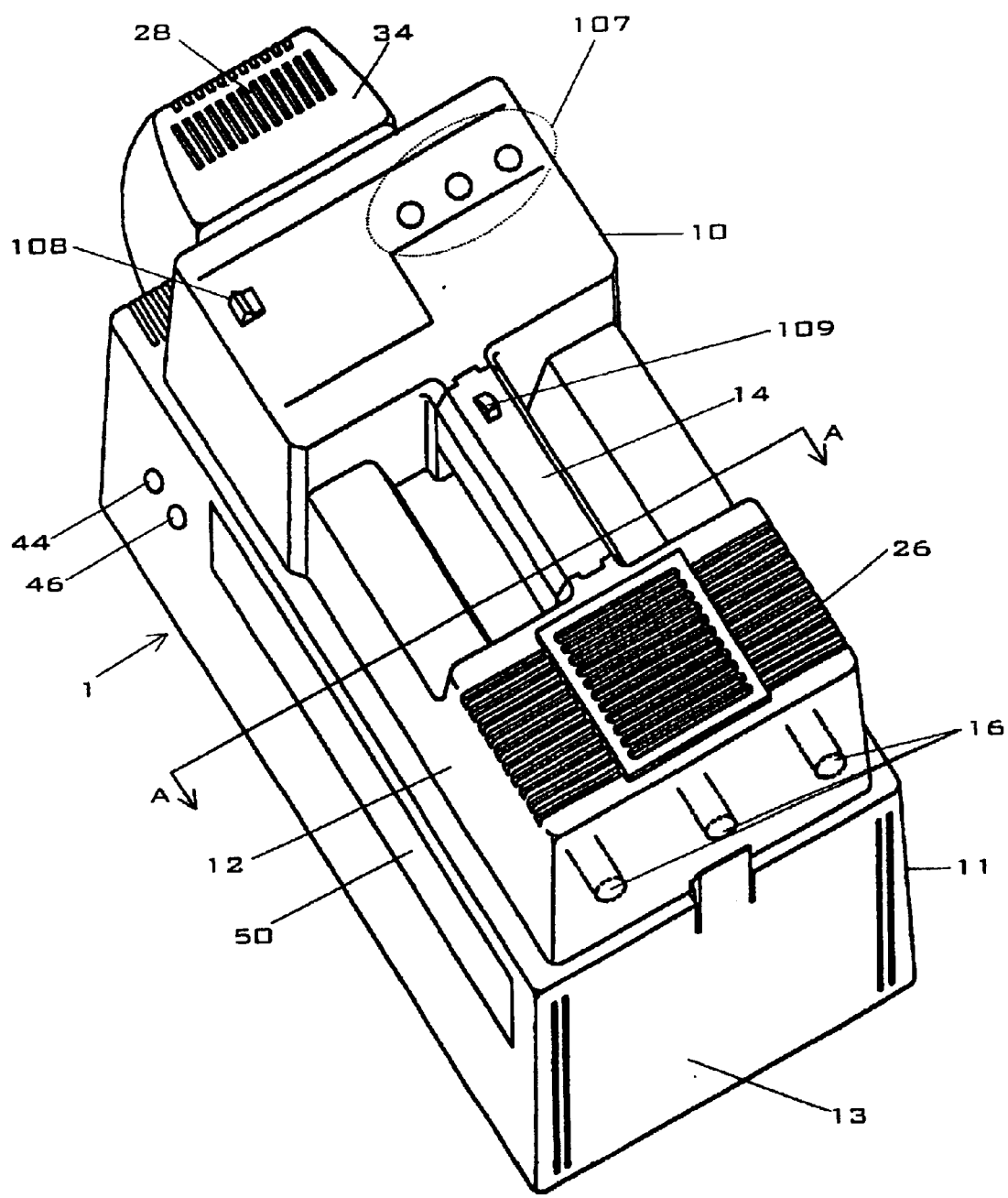
FIG. 1 is a perspective view showing an embodiment of the present invention.

1 Apparatus
10 Hand-held unit
11 Base unit
12 Housing
13 Housing
14 Handle
16 Lamp
17 Reflective surface
18 Grid
19 Open end
20 Open end
26 Aperture
28 Vent
30 Plug unit
32 Socket
34 Fan
40 Unitary apparatus
42 Mail
44 Eject button
46 Retract button
47 Motor
48 Switch
49 Removable cover
50 Receptacle
51 Drive wheel
52 Handle
54 Reflector
56 Cover
57 Top surface
58 Tray
59 Bottom surface
60 Object
61 Tray length
62 Guide
63 Tray depth
64 Contoured reflector
66 Bulb socket
67 Cover height
70 Chamber
72 Lamp
100 Power cord
101 Charger
102 Special connector
103 Ion generator 105 Ballast
107 Indicator panel
108 Lamp switch
109 Safety switch
110 Rechargeable battery

SUMMARY OF INVENTION

An object of the present invention is to provide for the neutralization of chemical and biological threats.

Another object of the present invention is to provide for the complete decontamination of the exterior of an object without a reorientation of the object.

A further object of the present invention is to provide for the contained decontamination of high-risk items, examples including but not limited to mail and money.

The present invention is an apparatus, sufficiently capable of neutralizing agents and organisms adhered to an object, having a slidable tray facilitating the insertion of a contaminated object into and the removal of a decontaminated object from the apparatus. In preferred embodiments, a handle is attached to the exterior of the receptacle thereby enabling the user to manually extend and retract the receptacle. In other embodiments, the receptacle is mechanically extended and retracted via a motor. In still other embodiments, hand-held and base units are fixed so that hand-held unit is not removable from base unit, thereby forming a unitary construction for the contained decontamination of objects. In yet other embodiments, a switch is fixed to the apparatus thereby contacting the receptacle so as to allow activation of lamps when tray is retracted and prevent activation of lamps when tray is extended.

The present invention incorporates germicidal and thermal tubes to neutralize chemical agents and/or biological organisms. Thermal tubes generate heat sufficient to degrade chemical agents. Germicidal tubes alone or in combination with one or more thermal tubes are generally more effective against weaponized organisms, one example being anthrax. In preferred embodiments, both germicidal and thermal tubes are provided about the tray. In alternate embodiments, germicidal and thermal tubes are provided along one surface of the tray and a contoured reflective element is provided opposite of the other surface so to maximize light and/or heat energies deposited onto the object.

Several advantages are noteworthy for the present invention. The apparatus provides a mechanical means, namely a tray, for inserting and extracting an object from the interior of the apparatus thereby minimizing exposure to the object during the decontamination process. Receptacle design prevents exposure to the user by ultraviolet radiation during the decontamination process. Tray design in conjunction with lamps and lamp-reflector arrangements about the tray insures the deposition of radiation and heat onto the exterior of the object. The invention provides two neutralizing mechanisms, namely thermal and radiation energies, thereby more effectively eliminating a wider range of threats.

DESCRIPTION OF THE INVENTION

Referring to FIG. 1, an embodiment of the present invention is shown integrated into a device comprised of a hand-held unit 10 and a base unit 11.

The hand-held unit 10 is powered by a rechargeable battery 110 and comprised of a housing 12 having at least one lamp 16, apertures 26, a grid 18, an indicator panel 107, a lamp switch 108, a safety switch 109, and a socket 32. A handle 14 is attached to or molded onto the hand-held unit 10 along the exterior of the housing 12 thereby enabling a user to move the hand-held unit 10 in a controlled fashion over a surface when detached from the base unit 11. Decontamination energy generated by the lamps 16 is deposited onto a surface exposed thereto.

Figure 2:
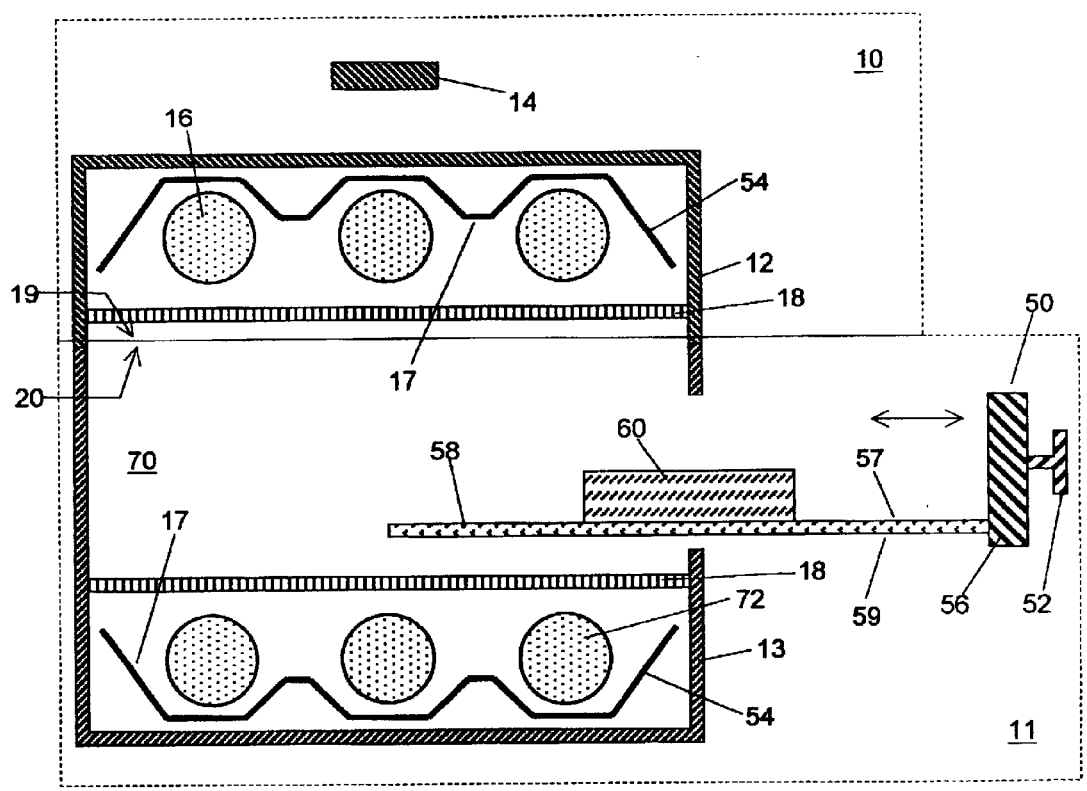
FIG. 2 is an illustrative sectional view showing lamp within hand-held and base units with receptacle extended from base unit.

Referring now to FIG. 2, the housing 12 is manufactured from a lightweight material, preferably a plastic. While various shapes are possible for the housing 12, preferred embodiments are box-like and rectangular in shape having one open end 19. One or more lamps 16 are fixed within the housing 12 and electrically connected to lamp switch 108, safety switch 109, indicator panel 107, socket 32, and rechargeable battery 110. The grid 18 is attached via fasteners to the housing 12 opposite of the lamps 16 so as to provide a protective envelope around the lamps 16. A reflector 54 fixed within the housing 12 between housing 12 and lamps 16 redirects that portion of radiation and heat energies otherwise reaching the housing 12.

The base unit 11 is comprised of a housing 13 having a vent 28, a fan 34, a plug unit 30, an eject button 44, and a retract button 46, as shown in FIG. 1. Referring again to FIG. 2, the housing 13 is manufactured from a lightweight material having a box-like shape with one open end 20. The hand-held unit 10 is removably secured to the base unit 11 so that both open ends 19, 20 are joined to form a single chamber 70. The fan 34 draws air through apertures 26, molded or mechanically inserted into the housing 12, into and across the chamber 70. Air currents interact with lamps 16 thereby neutralizing agents or organisms contained therein and thereafter expelled through the vent 28. Air flow prevents overheating of lamps 16 and other items within the chamber 70. While it is preferred to provide a fan 34 within the base unit 11 so as to reduce the weight of the hand-held unit 10, alternate embodiments may integrate the fan 34 into or provide a second fan 34 within the hand-held unit 10.

Figure 7:
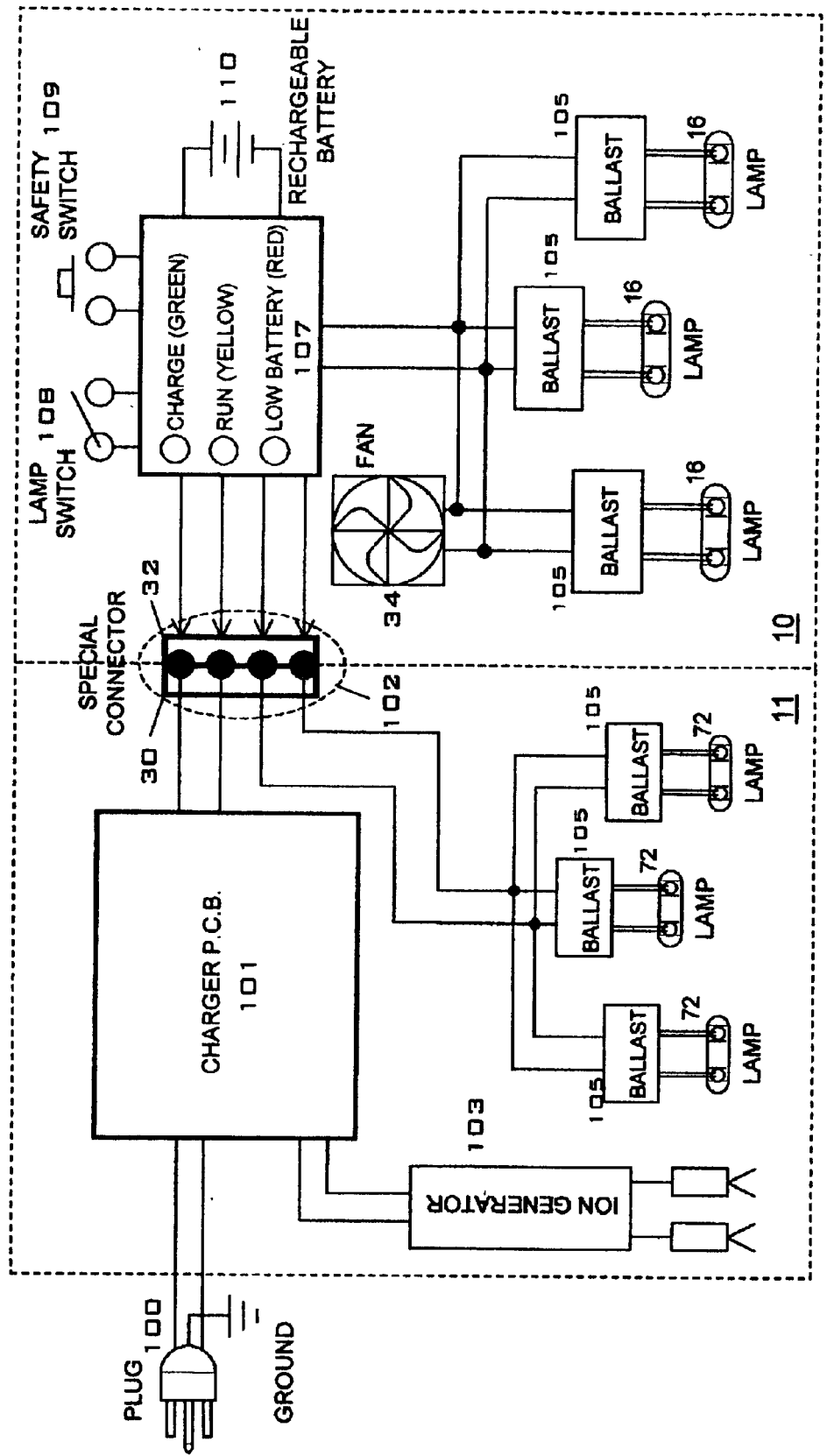
FIG. 7 shows an electrical block diagram for an embodiment of the present invention.

The socket 32 and plug unit 30 comprise the special connector 102 identified in FIG. 7 and are mechanically attached to the respective housings 12, 13 so that a complete electrical connection is achieved when hand-held unit 10 is seated onto the base unit 11. Socket 32 and plug unit 30 communicate electrical power and functionality between hand-held unit 10 and base unit 11.

FIGS. 2–5 show a preferred embodiment of the present invention having a receptacle 50 and two sets of lamps 16, 72. The receptacle 50 facilitates insertion of an object 60 into and removal of the same object 60 from the chamber 70 formed between housings 12, 13.

Figure 4:
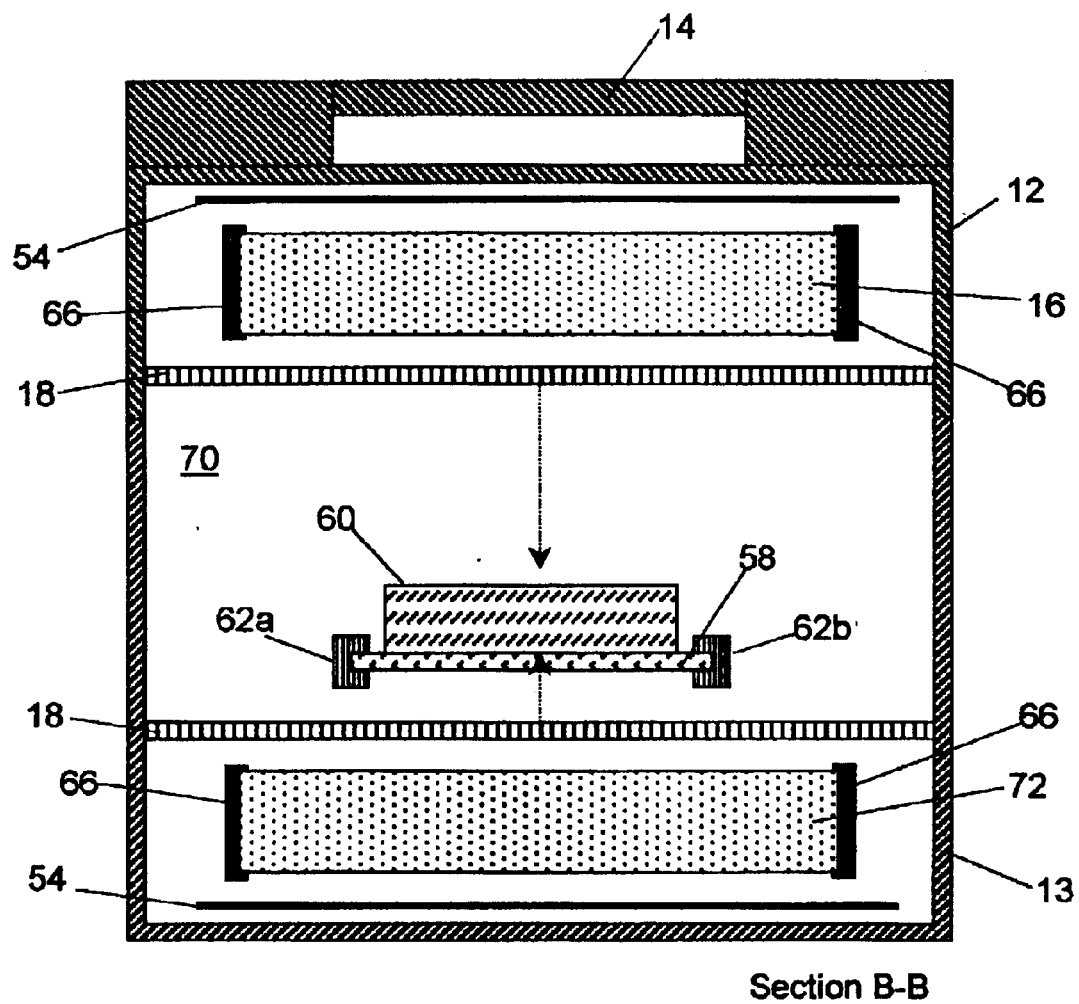
FIG. 4 is an illustrative sectional view showing tray aligned between guides.

Referring again to FIG. 2, the receptacle 50 is slidably disposed between one or more lamps 16 arranged above the top surface 57 of the tray 58 and one or more lamps 72 arranged below the bottom surface 59 of the same tray 58. Lamps 16, 72 are secured to their respective housings 12,13 via bulb sockets 66, as shown in FIG. 4, and thereafter electrically connected to lamp switch 108, safety switch 109, socket 32, plug unit 30, and rechargeable battery 110.

Lamps 16, 72 may include germicidal tubes, thermal or heating tubes, and combinations thereof. For example, a germicidal tube is a commercially available device understood in the art that emits ultraviolet radiation, preferably UV-C at a wavelength of 253.7 nanometers. Whereas, a heating tube is a commercially available device understood in the art that heats air adjacent to the tube. Preferred embodiments of the present invention require the heating tube to generate an air temperature of at least 160 C.

Figure 3:
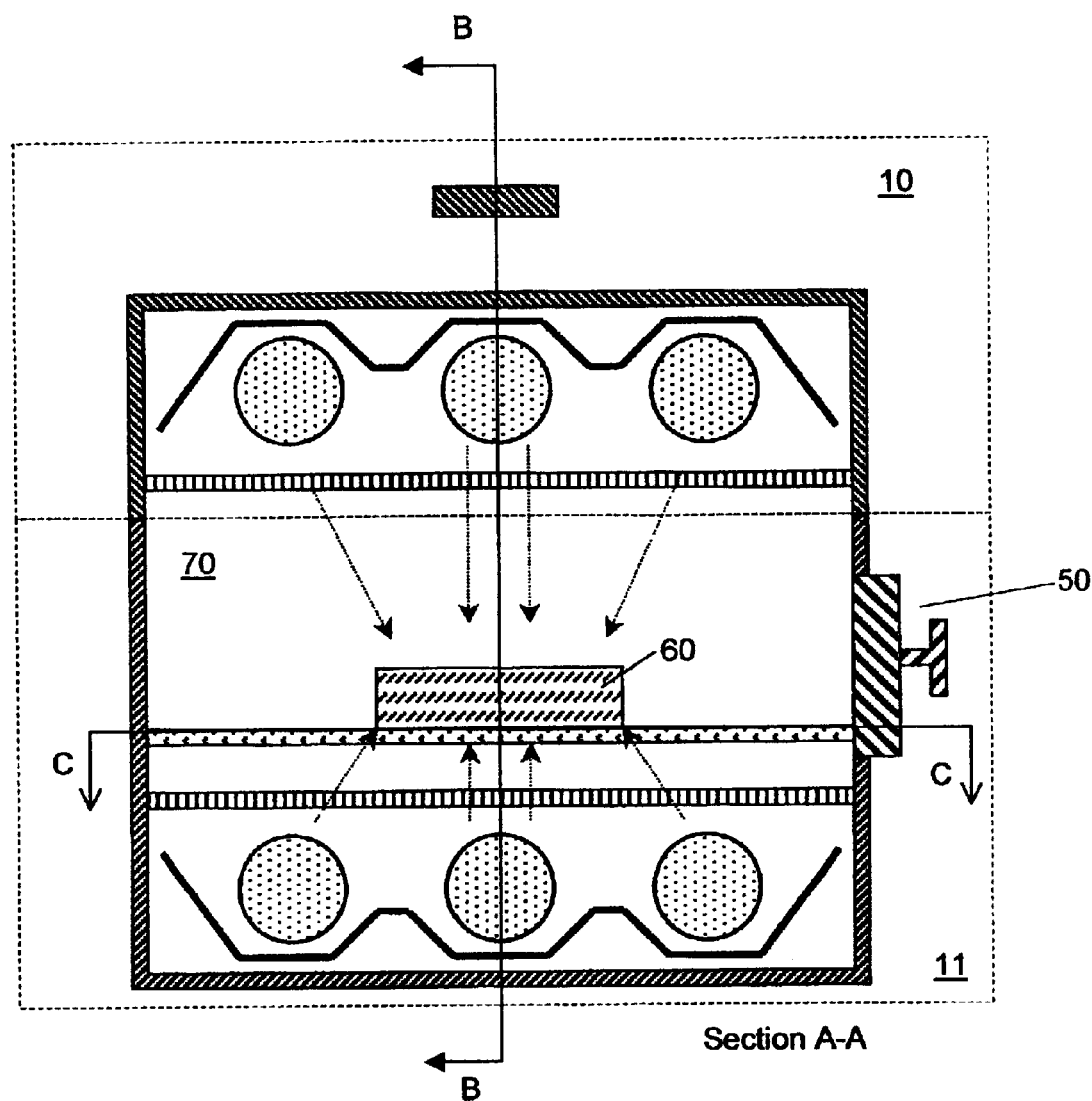
FIG. 3 is an illustrative sectional view showing receptacle retracted into base unit.

While various arrangements are possible, one such configuration includes two or more lamps 16, 72 disposed in a parallel arrangement having at least one germicidal tube and one heating tube. FIGS. 2–4 show an apparatus 1 having three lamps 16 within the hand-held unit 10 and three lamps 72 within the base unit 11. FIG. 3 graphically depicts the path of neutralizing energy deposited onto top, bottom, and sides of the object 60 by the preferred embodiment.

Referring again to FIG. 2, an exemplary receptacle 50 comprised of a cover 56 is attached in a perpendicular arrangement to a planar disposed tray 58. The receptacle 50 is shown extended from the base unit 11. The cover 56 is composed of a lightweight material sufficiently resistance to radiation and heat generated by lamps 16, 72 so as to contain said energies within the chamber 70. The cover 56 prevents access to the chamber 70 when receptacle 50 is retracted into the base unit 11 by closing a similarly dimensioned opening within the housing 13, as graphically depicted in FIG. 3. The tray 58 may be composed of a transparent glass or plastic, mesh, perforated element, or similarly disposed planar element allowing light and thermal energies to pass without appreciable degradation.

Extension and retraction of the receptacle 50 is performed manually via a handle 52 fixed to the cover 56 along the exterior of the apparatus 1, as shown in FIG. 3. However, the receptacle 50 may be mechanically controlled via a linear drive device, rotational motor, or comparable mechanism fixed within the base unit 11 and communicating with the receptacle 50.

Figure 8:
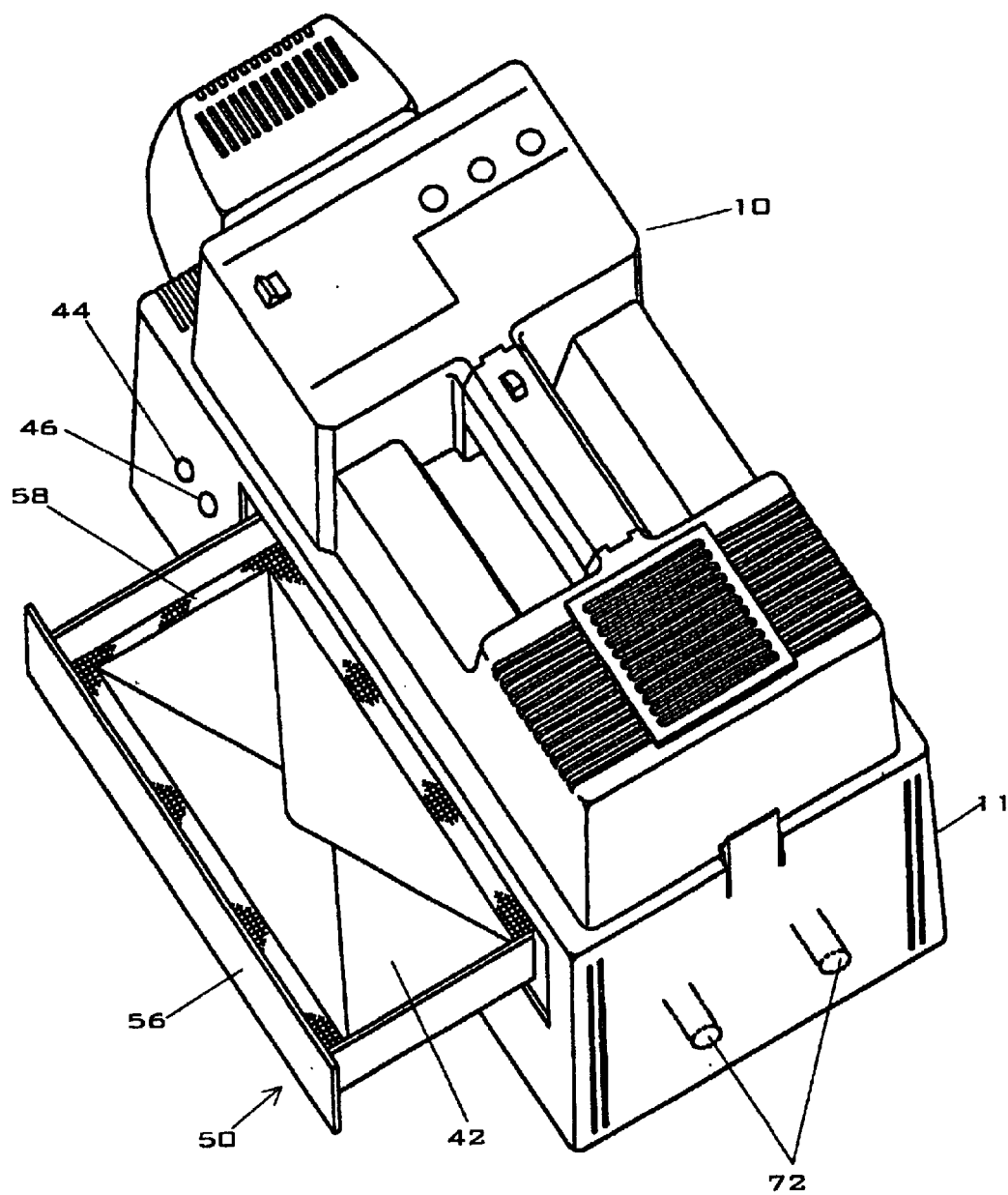
FIG. 8 is a perspective view showing receptacle extended from base unit.
Figure 12A:
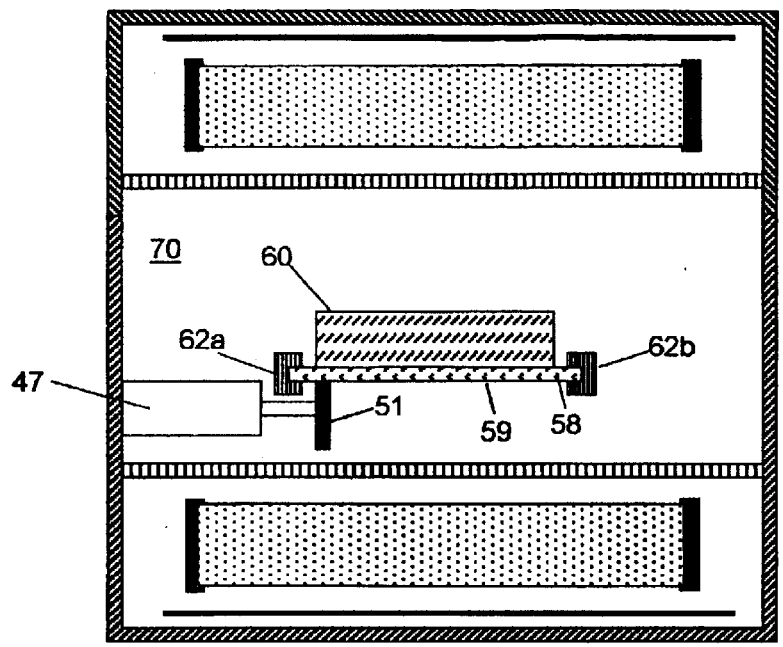
FIG. 12 is a drawing describing an exemplary embodiment of the motor controlled receptacle.
Figure 12B:
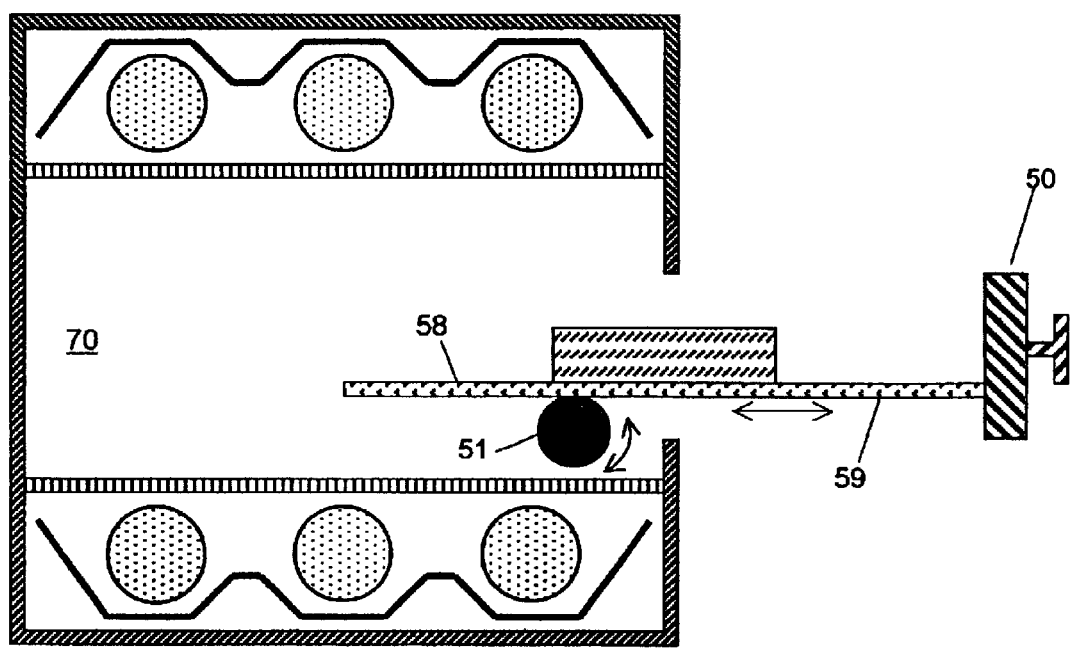

Referring now to FIGS. 12a–12b, one possible mechanically controlled receptacle 50 is shown wherein the tray 58 moves in a linear fashion when a drive wheel 51 is rotated. FIG. 12a shows a motor 47 fixed to the housing 13 and communicating with a drive wheel 51 contacting the bottom surface 59 of the tray 58. The drive wheel 51 is rotated by the motor 47 thereafter moving the tray 58 in a linear fashion, as depicted in FIG. 12b. The motor 47 is electrically attached to one or more control buttons mounted along the exterior of the apparatus 1. FIG. 1 shows an exemplary twin-button arrangement wherein an eject button 44 and a retract button 46 are mounted adjacent to the receptacle 50 shown in its retracted position. FIG. 8 shows the same embodiment wherein the receptacle 50 is extended from the base unit 11 after depression of the eject button 44. Alternatively, eject and retract movement may be activated by a single button with two-step functionality.

Figure 9:
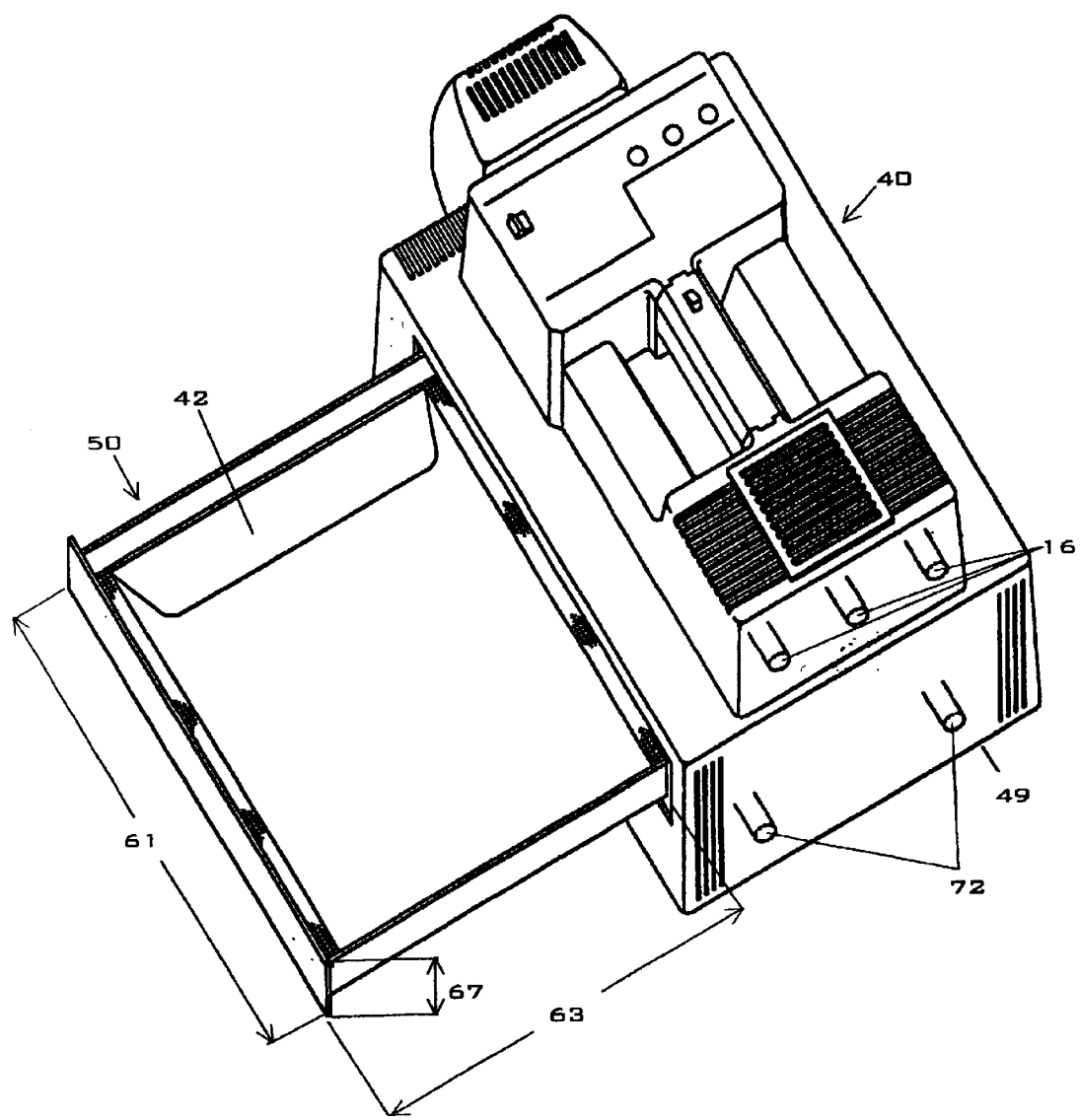
FIG. 9 is a perspective view of unitary apparatus with receptacle extended and supporting an envelope.

Referring now to FIG. 9, receptacle 50 dimensions are application dependent. For example, a tray length 61 of eleven inches and a tray depth 63 of five inches is sufficient to accommodate the decontamination of most mail 42 and other high-risk items encountered in a residential setting. A two-inch cover height 67, and correspondingly dimensioned chamber 70, is sufficient to accommodate small box-like items, although a dimensionally larger receptacle 50 may be required for parcels encountered in a commercial setting.

Referring again to FIG. 2, preferred embodiments of the present invention have at least one lamp 72 within the base unit 11 located between a grid 18 and a reflector 54. The grid 18 is secured to the housing 13 as described above. A reflector 54 is mechanically fastened to the housing 13, as well as to the interior of the housing 12 as shown. Each reflector 54 has a sufficiently reflective surface 17 so as to redirect light and thermal energy away from the housings 12, 13, through the grid 18, and onto the object 60. A three lamp 16, 72 arrangement was found to be sufficient to completely expose letter size mail 42 to decontaminating UV radiation and heat.

Figure 5:
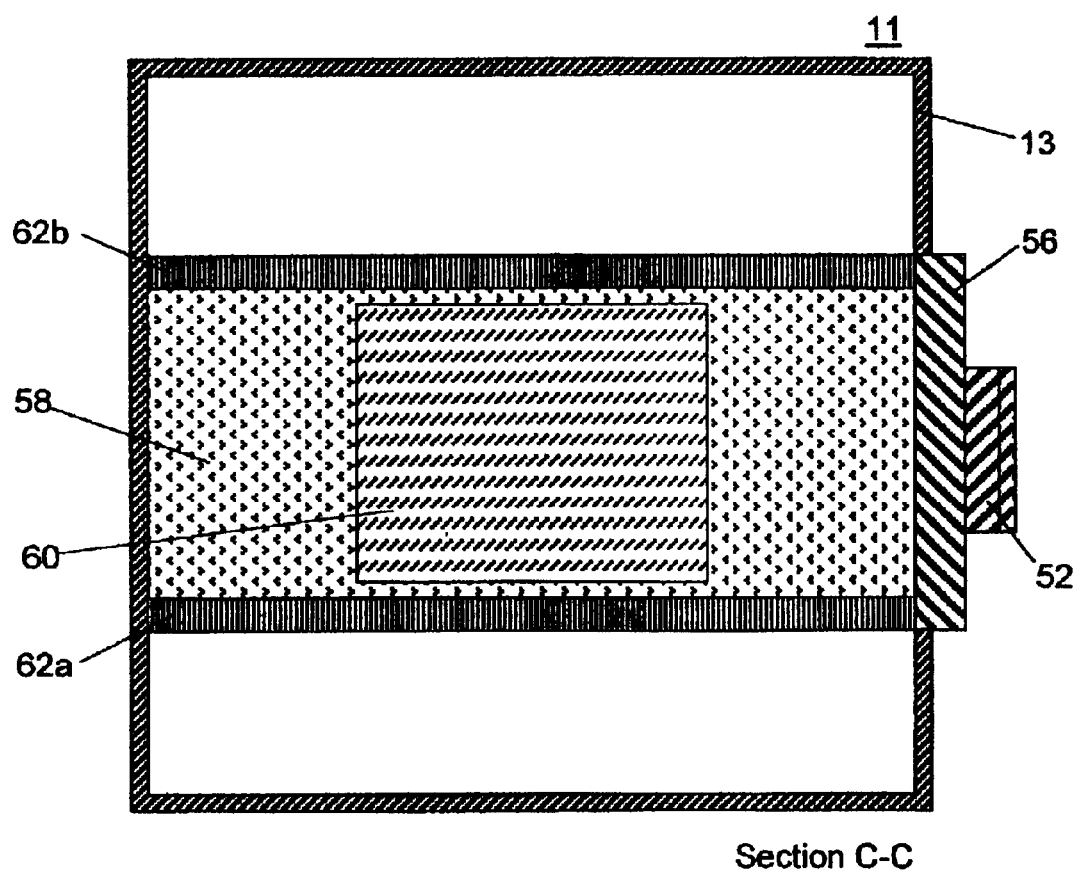
FIG. 5 is an illustrative sectional view showing top surface of receptacle supporting an object.

Referring now to FIGS. 4–5, an object 60 is shown resting on the top surface 57 of the tray 58. The depth-wise disposed edges of the tray 58 contact a pair of oppositely disposed c-shaped guides 62a, 62b, as shown in FIG. 4. Guides 62 are mechanically fastened to the housing 13 so as to prevent their movement thereby confining the tray 58. The sliding movement of the tray 58 is restricted to a plane aligned with the guides 62a, 62b. Guides 62a, 62b are preferably manufactured from a low-friction material or having a low-friction surface so as to facilitate the desired sliding motion by the tray 58. Receptacle 50 motion may be limited by tabs, positive stops, limit switches, or other similar devices between tray 58 and guides 62a, 62b.

Figure 6:
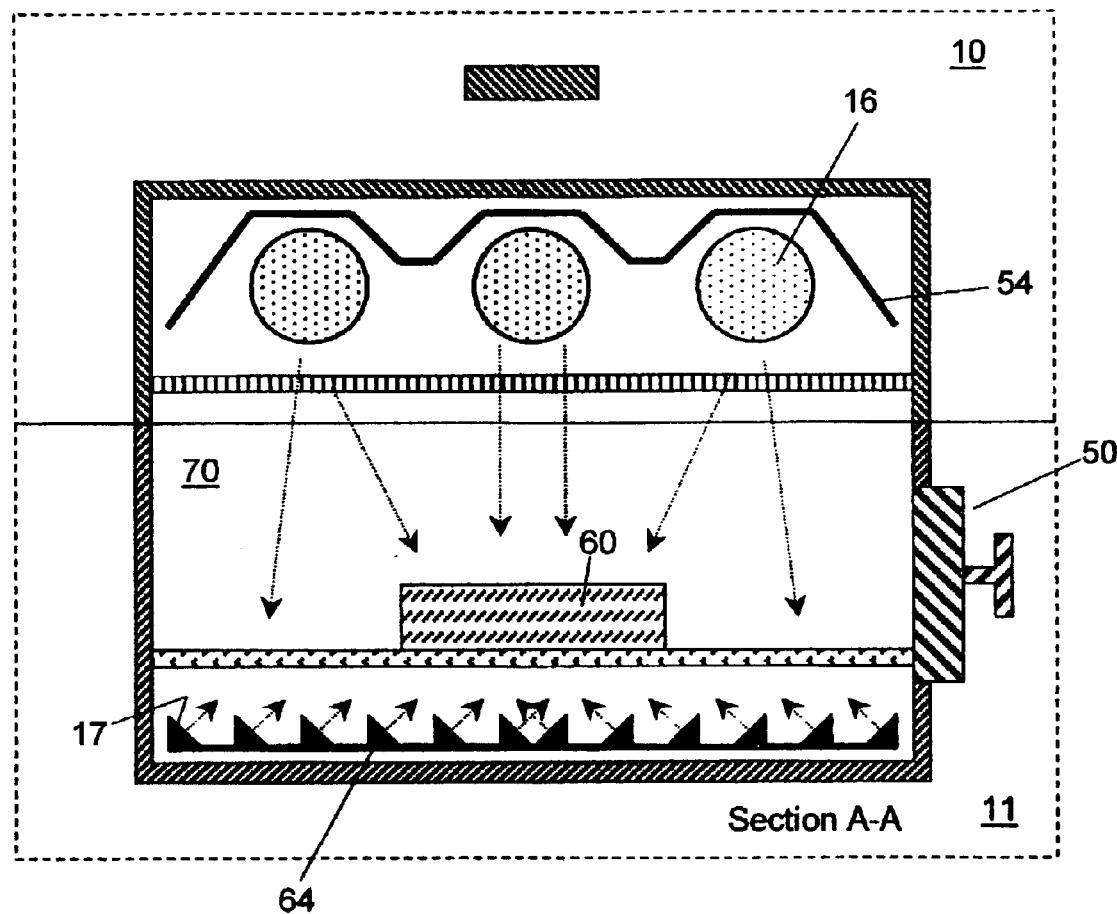
FIG. 6 is an illustrative section view of an embodiment having lamps within hand-held unit and a contoured reflector within base unit.

Referring now to FIG. 6, an alternate embodiment is shown having several lamps 16 within the hand-held unit 10 and a contoured reflector 64 attached to the housing 13 comprising the base unit 11. In this configuration, decontamination energy produced by the lamps 16 is projected downward towards the object 60, a portion of which passes uninterrupted. This uninterrupted energy is thereafter reflected by the contoured reflector 64 and directed towards the bottom and sides of the object 60. While various designs are possible for the contoured reflector 64, the element functionally redirects and focuses energy that might otherwise not reach the object 60. Exemplary designs for the contoured reflector 64 include but are not limited to a textured surface and/or a precisely contoured geometry. FIG. 6 specifically, describes one possible embodiment comprised of spaced right triangles, each having a reflective surface 17 and spanning the length of the base unit 11. It is likewise possible that the contoured reflector 64 be comprised of a two-dimensional or a three-dimensional concave profile having a reflective surface 17 directed towards the object 60. The contoured reflector 64 may be manufactured from a polished metal, a mirror-like material, or a plastic with thin-film reflective coating.

Referring now to FIG. 7, a block diagram is shown for an exemplary embodiment of present invention.

The base unit 11 has a power cord 100 electrical connected to a charger 101 and thereafter to the plug unit 30 of a multi-contact special connector 102 and an optional ion generator 103. The power cord 100 communicates AC voltage from an external source to the charger 101 wherein it is converted to DC voltage. The ion generator 103 emits ions which further facilitate the removal of organic particles from the air stream. Additionally, the base unit 11 has at least one lamp 72, each attached to a ballast 105.

The hand-held unit 10 is comprised of an indicator panel 107 electrically connected to a lamp switch 108, a safety switch 109, a rechargeable battery 110, at least one lamp 16, and an optional fan 34. When detached from the base unit 11, lamps 16 and fan 34 are activated by communicating power from the rechargeable battery 110 by engaging both lamp switch 108 and safety switch 109. When attached to the base unit 11, contact between socket 32 and plug unit 30 is achieved, thereby facilitating current flow from the rechargeable battery 110 to lamps 72. Operation of lamp switch 108 and safety switch 109 in the attached configuration provides current flow to both sets of lamps 16, 72 and in 34. In some embodiments, fan 34 function may not be desired when the apparatus 1 is employed to decontaminate objects 60 within the chamber 70 and therefore would not be activated.

Figure 10:
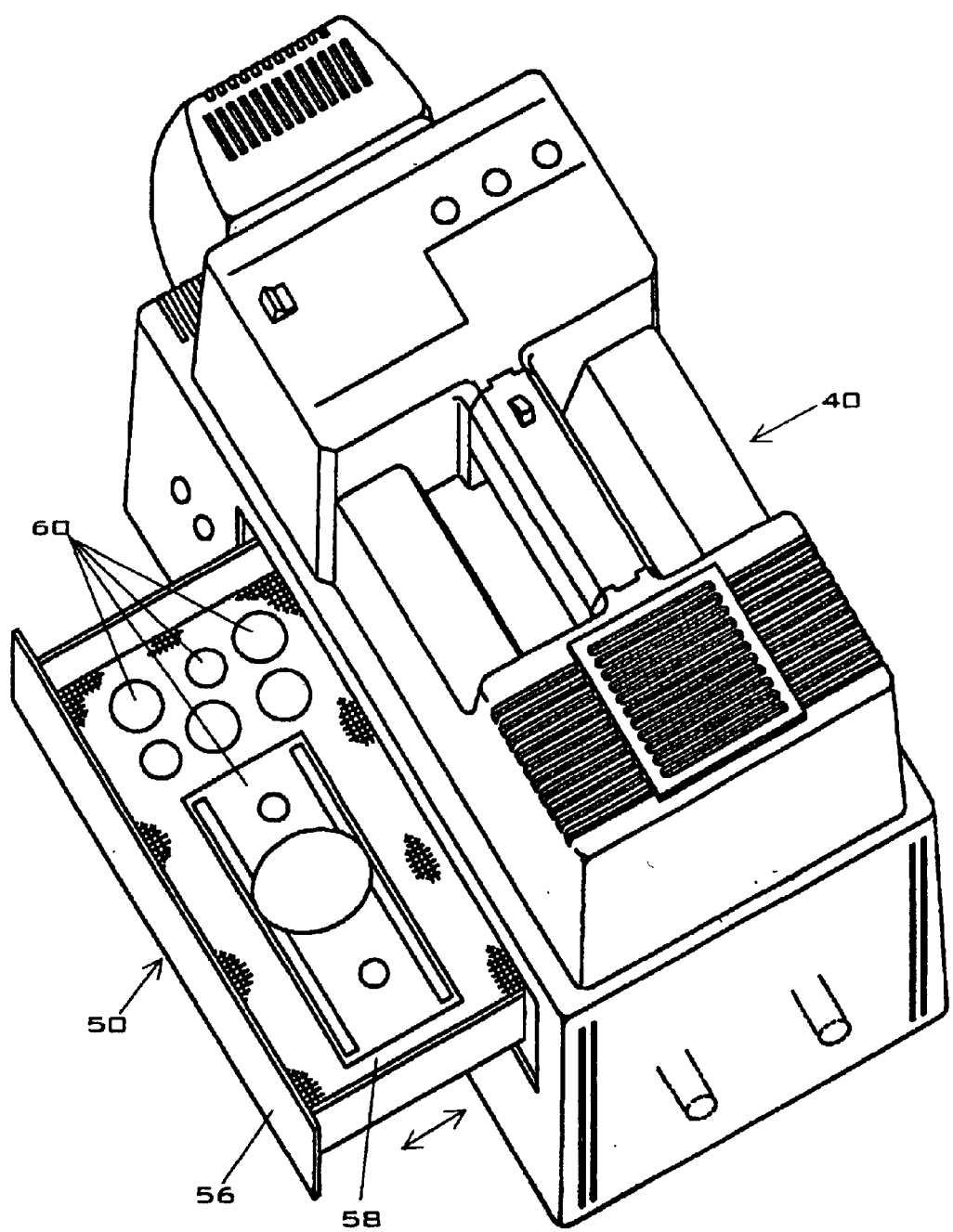
FIG. 10 is a perspective view of unitary apparatus with receptacle extended and supporting several objects.

Referring now to FIGS. 9–10, the present invention may be comprised of a single-piece unit wherein hand-held unit 10 and base unit 11 are molded, formed, or joined so that a unitary apparatus 40 is provided. In this embodiment, housings 12 and 13 are molded from a polymer resin or molded independently and thereafter mechanically attached or connected so that the hand-held functionality described above is not possible. Mechanical and electrical components identified above are assemble into the unitary apparatus 40 as described. A removable cover 49 comprised of a plate-shaped element is mechanically fastened to the bottom of the unitary apparatus 40 to facilitate access to the chamber 70 for maintenance purposes. Mail 42 and other objects 60 are inserted into the chamber 70 via the receptacle 50 as described.

Functionality of lamps 16, 72 may be controlled either by the lamp switch 108 and safety switch 109 arrangement described above or via a switch 48 mounted within the chamber 70. Representative switches 48 include mechanical devices, one example being a contact type, and optical devices, one example being a light-sensor pair, both understood within the art.

Figure 11A:
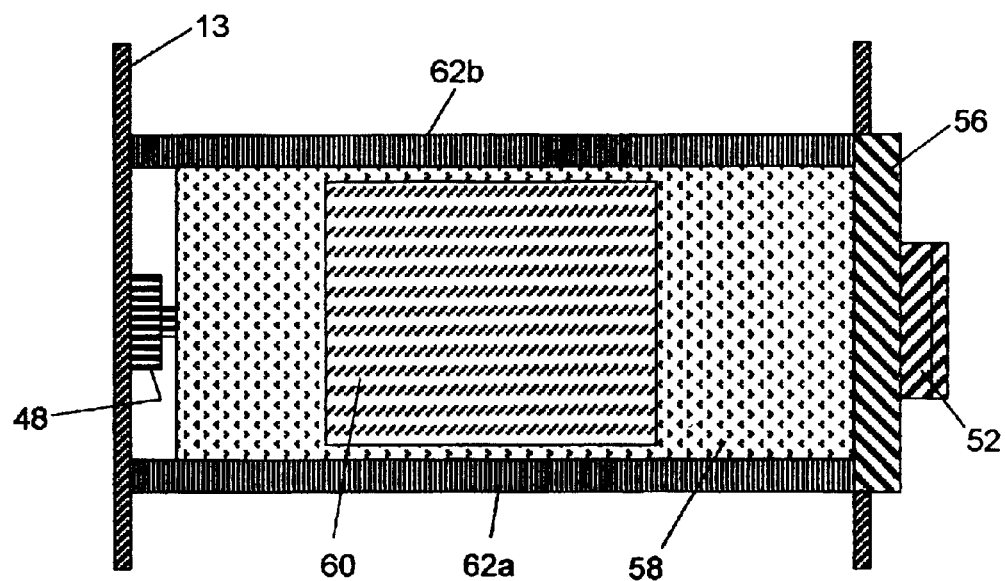
FIG. 11 is a drawing describing an exemplary embodiment of the switch arrangement.
Figure 11B:
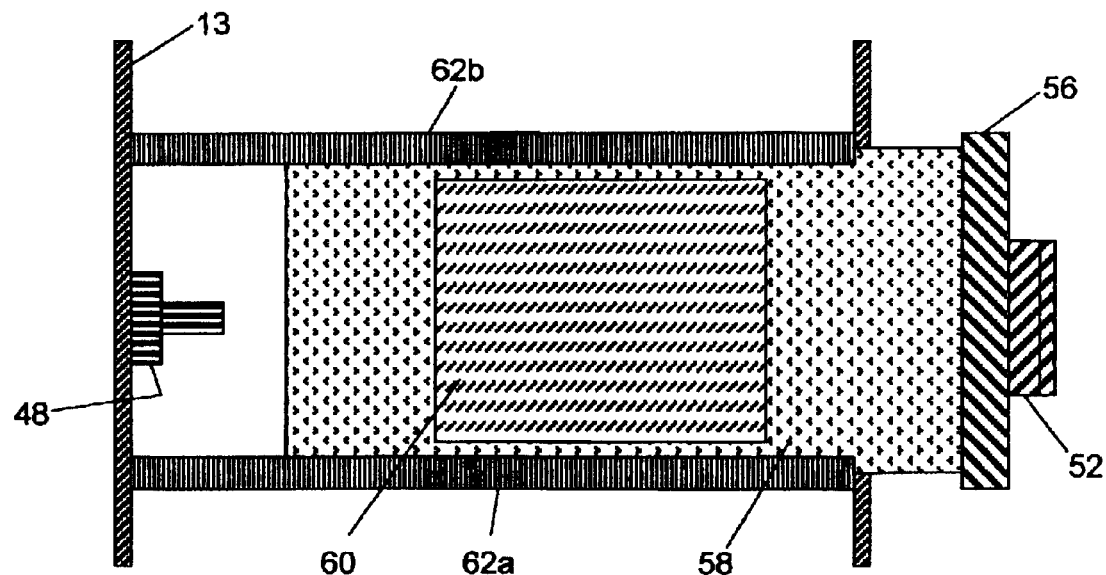

Referring now to FIGS. 11a–11b, a mechanically operable depression-type switch 48 is shown fixed to the housing 13 and positioned so that the tray 58 contacts the switch 48 when the tray 58 is retracted into the chamber 70. While a variety of switching options are possible, FIG. 11a shows the tray 58 retracted into the chamber 70 so as to contact the switch 48 thereby enabling the function of lamps 16, 72 within the chamber 70. FIG. 11b shows the tray 58 extended from the chamber 70 so as to not contact the switch 48 thereby deactivating lamps 16, 72 within the chamber 70. The described switch 48 may also functionally disable the described lamp switch 108 or communicate to a timer element controlling the ON time of the lamps 16, 72. It is also possible to employ the switch 48 so as to eject the receptacle 50 upon completion of the decontamination cycle.

The description above indicates that a great degree of flexibility is offered in terms of the described invention. Although the present invention has been described in considerable detail with reference to certain preferred versions thereof, other versions are possible. Therefore, the spirit and scope of the appended claims should not be limited to the description of the preferred versions contained herein.

What is claimed is:

1. An apparatus for neutralizing chemical and biological threats contaminating an object comprising:
   (a) a chamber disposed within said apparatus, said chamber sufficiently voluminous to accommodate insertion of said object;
   (b) at least one heat lamp within said chamber generating thermal energy to degrade said chemical and biological threats;
   (c) at least one germicidal lamp within said chamber generating radiation energy to neutralize said chemical and biological threats; and
   (d) a receptacle extensible from and retractable into said chamber, said receptacle having a cover attached to a tray horizontally disposed within said chamber having a top surface and a bottom surface, said tray supporting said object along said top surface so as to allow degradation of said chemical and biological threats by said heat lamps and neutralization of said chemical and biological threats by said germicidal lamps, said cover containing emissions from said germicidal lamps within said apparatus when said receptacle is retracted.

2. The apparatus as in claim 1, wherein said at least one heat lamp and said at least one germicidal lamp are disposed adjacent to said top surface and said bottom surface.

3. The apparatus as in claim 1, wherein said at least one heat lamp and said at least one germicidal lamp are disposed adjacent to said top surface.

4. The apparatus as in claim 3, further comprising a contoured reflector adjacent to said bottom surface so as to redirect a portion of said emissions from said at least one heat lamp and said at least one germicidal lamp onto said object.

5. The apparatus as in claim 1, wherein said at least one heat lamp and said at least one germicidal lamp are arranged adjacent to said bottom surface.

6. The apparatus as in claim 5, further comprising a contoured reflector adjacent to said top surface so as to redirect a portion of said emissions from said at least one heat lamp and said at least one germicidal lamp onto said object.

7. The apparatus as in one of claims 1–6, further comprising a switch fixed to said apparatus so as to control function of said at least one heat lamp and said at least one germicidal lamp based upon position of said receptacle.

8. The apparatus as in one of claims 1–6, wherein movement of said receptacle is manually operable.

9. The apparatus as in one of claims 1–6, wherein movement of said receptacle is mechanically operable.

* * * * *